(12) United States Patent
Nishiyama et al.

(10) Patent No.: US 12,357,420 B2
(45) Date of Patent: Jul. 15, 2025

(54) CLEANING SUPPORT SYSTEM, PROCESSING APPARATUS, AND CLEANING SUPPORT METHOD

(71) Applicant: OLYMPUS CORPORATION, Tokyo (JP)

(72) Inventors: Takeshi Nishiyama, Tokyo (JP); Akira Suzuki, Tokyo (JP); Hideyuki Kugimiya, Tokyo (JP); Yumiko Awau, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 542 days.

(21) Appl. No.: 17/228,792

(22) Filed: Apr. 13, 2021

(65) Prior Publication Data
US 2021/0298871 A1    Sep. 30, 2021

Related U.S. Application Data

(63) Continuation of application No. PCT/JP2018/038669, filed on Oct. 17, 2018.

(51) Int. Cl.
*A61B 90/70* (2016.01)
*A61B 1/00* (2006.01)
(Continued)

(52) U.S. Cl.
CPC .......... *A61B 90/70* (2016.02); *A61B 1/00057* (2013.01); *A61B 1/122* (2013.01);
(Continued)

(58) Field of Classification Search
CPC .............. A61B 90/70; A61B 2090/701; A61B 1/00059; A61B 1/00057; A61B 1/122;
(Continued)

(56) References Cited

U.S. PATENT DOCUMENTS

2001/0041825 A1*  11/2001  Shibata .............. A61B 1/00059
                                                        600/118
2007/0286764 A1*  12/2007  Noguchi ............ A61B 1/00059
                                                        422/62

FOREIGN PATENT DOCUMENTS

JP    2009279193 A  * 12/2009
JP    2012239536 A  * 12/2012
(Continued)

OTHER PUBLICATIONS

International Search Report and Written Opinion of the International Searching Authority mailed Jan. 8, 2019 received in PCT/JP2018/038669.

*Primary Examiner* — Amandeep Saini
*Assistant Examiner* — Daniella M. DiGuglielmo
(74) *Attorney, Agent, or Firm* — Scully, Scott, Murphy & Presser, P.C.

(57) ABSTRACT

Based on image data obtained by imaging a state of the preliminary cleaning of an endoscope by manual work, a cleaning status determination unit determines whether or not the preliminary cleaning has been performed on the endoscope. A notification control unit generates notification data regarding the determination result in the cleaning status determination unit and outputs the notification data from the output apparatus. When the cleaning status determination unit identifies a step that has not been properly performed, the notification control unit generates notification data including information regarding the step that has not been properly performed. The notification control unit may generate notification data including image data obtained by imaging the state of the step.

21 Claims, 10 Drawing Sheets

(51) Int. Cl.
*A61B 1/12* (2006.01)
*G06V 20/52* (2022.01)
*G08B 5/22* (2006.01)
*G08B 21/24* (2006.01)

(52) U.S. Cl.
CPC ............... *G06V 20/52* (2022.01); *G08B 5/22* (2013.01); *G08B 21/245* (2013.01); *A61B 1/00059* (2013.01); *A61B 1/123* (2013.01); *A61B 2090/701* (2016.02)

(58) Field of Classification Search
CPC .......... A61B 1/123; G06V 20/52; G08B 5/22; G08B 21/245
See application file for complete search history.

(56) References Cited

FOREIGN PATENT DOCUMENTS

| | | | |
|---|---|---|---|
| JP | 2014014524 A | * | 1/2014 |
| JP | 2017-000441 A | | 1/2017 |
| JP | 2017131335 A | * | 8/2017 |

* cited by examiner

FIG.3

WATER LEAKAGE TEST

A1 PREPARE A WATER LEAKAGE TEST CONTAINER AND FILL IT WITH WATER.

A2 INSERT A CONNECTOR FOR A WATER LEAKAGE TESTER INTO THE MAINTENANCE UNIT, TURN ON THE POWER SWITCH OF THE MAINTENANCE UNIT, AND SET THE AIR FEED PRESSURE TO "HIGH".

A3 LIGHTLY PRESS A ROD INSIDE THE MOUNTING BASE OF THE WATER LEAKAGE TESTER AND CHECK THAT THE AIR COMES OUT.

A4 ATTACH THE MOUNTING BASE OF THE WATER LEAKAGE TESTER TO THE VENTILATING BASE OF THE SCOPE CONNECTOR PART.

A5 IMMERSE THE ENDOSCOPE MAIN UNIT TO WHICH THE WATER LEAKAGE TESTER IS ATTACHED IN THE CONTAINER AND CHECK THAT CONTINUOUS AIR BUBBLES ARE NOT GENERATED FROM THE ENDOSCOPE MAIN UNIT FOR ABOUT 30 SECONDS WHILE BENDING THE CURVED PART OF THE ENDOSCOPE MAIN UNIT.

A6 PULL OUT THE ENDOSCOPE MAIN UNIT AND THE WATER LEAKAGE TESTER.

A7 TURN OFF THE POWER OF THE MAINTENANCE UNIT.

A8 REMOVE THE CONNECTOR FOR THE WATER LEAKAGE TESTER FROM THE MAINTENANCE UNIT.

A9 WAIT FOR ABOUT 30 SECONDS UNTIL BULGING OF THE COVERING RUBBER AT THE CURVED PART DISAPPEARS AND REMOVE THE CONNECTOR FOR THE WATER LEAKAGE TESTER FROM THE VENTILATING BASE OF THE SCOPE CONNECTOR PART.

A10 DRY THE WATER LEAKAGE TESTER.

MANUAL CLEANING

CLEANING OF OUTER SURFACE

B1 PREPARE A CONTAINER FOR A CLEANING LIQUID WITH A LID AND FILL THE CONTAINER WITH A CLEANING LIQUID ADJUSTED TO HAVE THE TEMPERATURE AND CONCENTRATION INSTRUCTED BY THE MANUFACTURER OF THE CLEANING LIQUID.

B2 IMMERSE THE ENDOSCOPE MAIN UNIT IN THE CLEANING LIQUID.

B3 WIPE THE TIP OF THE INSERTION PART AND THE OUTER SURFACE OF THE ENDOSCOPE MAIN UNIT IN THE CLEANING LIQUID USING A SPONGE, GAUZE, PAPER TOWEL, OR THE LIKE. SPECIFICALLY, WIPE THE AIR/WATER SUPPLY NOZZLE OPENING AND THE LENS SURFACE (SEE REFERENCE FIGURE M).

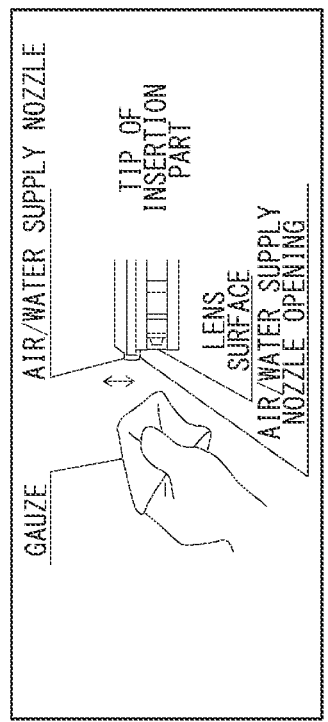

REFERENCE FIGURE M

MANUAL CLEANING
BRUSHING OF SUCTION CHANNEL IN INSERTION PART (POINT A)
C1 STRAIGHTEN THE CURVED PART OF THE ENDOSCOPE INSERTION PART AND HOLD A PART OF THE CHANNEL CLEANING BRUSH THAT IS ABOUT 3 CM FROM THE BRUSH PART.
C2 TILT THE CHANNEL CLEANING BRUSH 45 DEGREES TO THE SUCTION CYLINDER OPENING ON THE SIDE WALL OF THE SUCTION CYLINDER AND INSERT IT IN THE DIRECTION OF THE INSERTION PART (ARROW A IN A REFERENCE FIGURE N). PUSH THE BRUSH PART OUT OF THE EXIT OF THE ENDOSCOPE TIP FORCEPS.
C3 WASH THE SOILED PART OF THE BRUSH PART BY HAND IN THE CLEANING LIQUID AND THEN PULL OUT THE BRUSH PART.
C4 AFTER PULLING OUT THE BRUSH PART, WASH THE SOILED PART OF THE BRUSH PART BY HAND IN THE CLEANING LIQUID AGAIN.
C5 REPEAT THE PROCEDURES IN C1 TO C4 AND KEEP THE BRUSHING UNTIL ALL THE DIRT IS REMOVED.

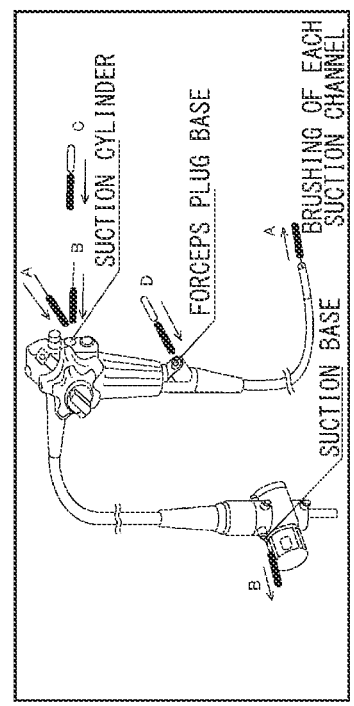

REFERENCE FIGURE N

FIG.6

MANUAL CLEANING
BRUSHING OF SUCTION CHANNEL IN UNIVERSAL CORD (POINT B)
D1 HOLD A PART OF THE CHANNEL CLEANING BRUSH THAT IS ABOUT 3 CM FROM THE BRUSH PART.
D2 INSERT THE BRUSH PART IN A STRAIGHT MANNER INTO THE SUCTION CYLINDER AND INSERT THE BRUSH PART IN THE DIRECTION OF THE UNIVERSAL CORD SO AS TO PUSH IT OUT OF THE SUCTION BASE OF THE SCOPE CONNECTOR (ARROW B IN THE REFERENCE FIGURE N).
D3 WASH THE SOILED PART OF THE BRUSH PART BY HAND IN THE CLEANING LIQUID AND THEN PULL OUT THE BRUSH PART.
D4 AFTER PULLING OUT THE BRUSH PART, WASH THE SOILED PART OF THE BRUSH PART BY HAND IN THE CLEANING LIQUID AGAIN.
D5 REPEAT THE PROCEDURES IN D1 TO D4 AND KEEP THE BRUSHING UNTIL ALL THE DIRT IS REMOVED.

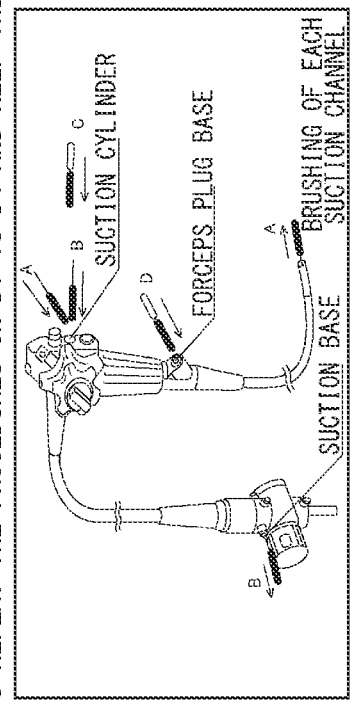

REFERENCE FIGURE N

13

THE ENDOSCOPE HAS NOT
BEEN PROPERLY CLEANED
MANUALLY IN THE STEP C2.
PLEASE RETRY THE STEP C2.

13

THE ENDOSCOPE HAS NOT BEEN PROPERLY
CLEANED IN THE STEP C2.
PLEASE RETRY THE STEP C2.
THE STATE OF THE MANUAL CLEANING IN
THE STEP C2 CAN BE CHECKED BY A MOVING IMAGE.

| EXAMINATION NUMBER | 0013 | 0018 |
|---|---|---|
| PATIENT ID | AAA | BBB |
| SCOPE ID | S1001 | S1001 |
| WORKER ID | U0025 | U0025 |
| EXAMINATION START TIME | 2018/9/28 10:00 | 2018/9/28 11:30 |
| EXAMINATION COMPLETION TIME | 2018/9/28 10:30 | 2018/9/28 12:00 |
| PRELIMINARY CLEANING START TIME | 2018/9/28 10:40 | 2018/9/28 12:05 |
| PRELIMINARY CLEANING COMPLETION TIME | 2018/9/28 10:50 | 2018/9/28 12:15 |
| MAIN CLEANING START TIME | 2018/9/28 10:55 | 2018/9/28 12:20 |
| MAIN CLEANING COMPLETION TIME | 2018/9/28 11:15 | 2018/9/28 12:50 |
| IMAGE DATA | FILE 1 | FILE 2 |

104

CLEANING SUPPORT SYSTEM, PROCESSING APPARATUS, AND CLEANING SUPPORT METHOD

CROSS-REFERENCE TO RELATED APPLICATIONS

This application is based upon and claims the benefit of priority from International Application No. PCT/JP2018/038669, filed on Oct. 17, 2018, the entire contents of which are incorporated herein by reference.

BACKGROUND

1. Field of the Disclosure

The present disclosure relates to a technology for supporting preliminary cleaning of endoscopes by cleaning workers.

2. Description of the Related Art

Japanese Unexamined Patent Application Publication No. 2017-441 discloses a cleaning work support system that displays a work instruction sheet showing a work procedure of a cleaning process corresponding to an object to be cleaned. In this cleaning work support system, the worker can move a display screen forward and backward by moving his/her hand in front of a motion sensor.

High-action disinfectants are used in endoscope cleaning apparatuses. However, protein residues such as mucus and blood of patients reduce the effectiveness of high-action disinfectants. Therefore, the cleaning worker performs a manual preliminary cleaning to remove protein residues before the main cleaning by an endoscope cleaning apparatus. However, the execution status of the preliminary cleaning is not currently managed.

SUMMARY

In this background, a purpose of the present disclosure is to provide a technology for managing the execution status of manual preliminary cleaning of endoscopes.

A cleaning support system according to one embodiment of the present disclosure includes: a cleaning status determination unit that determines whether or not preliminary cleaning has been performed on an endoscope based on image data obtained by imaging the state of the preliminary cleaning of the endoscope by manual work; and a notification control unit that generates notification data regarding the determination result in the cleaning status determination unit and outputs the notification data from an output apparatus.

A cleaning support method according to another embodiment of the present disclosure includes: determining whether or not preliminary cleaning has been performed on an endoscope based on image data obtained by imaging the state of the preliminary cleaning of the endoscope by a manual work; and generating notification data regarding the determination result and outputting the notification data from an output apparatus.

A cleaning support system according to another embodiment of the present disclosure includes: a notification control unit that generates notification data regarding the result of determining whether or not preliminary cleaning has been performed on an endoscope based on image data obtained by imaging the state of the preliminary cleaning of the endoscope by manual work and outputs the notification data from an output apparatus.

A processing apparatus according to another embodiment of the present disclosure includes: a cleaning status determination unit that determines whether or not preliminary cleaning has been performed on an endoscope based on image data obtained by imaging the state of the preliminary cleaning of the endoscope by manual work and outputs the determination result for the generation of notification data.

Optional combinations of the aforementioned constituting elements and implementations of the present disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 3 is a diagram showing a notification example for a water leakage test procedure;

FIG. 4 is a diagram showing a notification example for a procedure in the first stage of manual cleaning;

FIG. 5 is a diagram showing a notification example for a procedure in the second stage of the manual cleaning;

FIG. 6 is a diagram showing a notification example for a procedure in the third stage of the manual cleaning;

FIG. 11 is a diagram showing an example of information stored in a memory unit.

DETAILED DESCRIPTION

The disclosure will now be described by reference to the preferred embodiments. This does not intend to limit the scope of the present disclosure, but to exemplify the disclosure.

Figure 1:
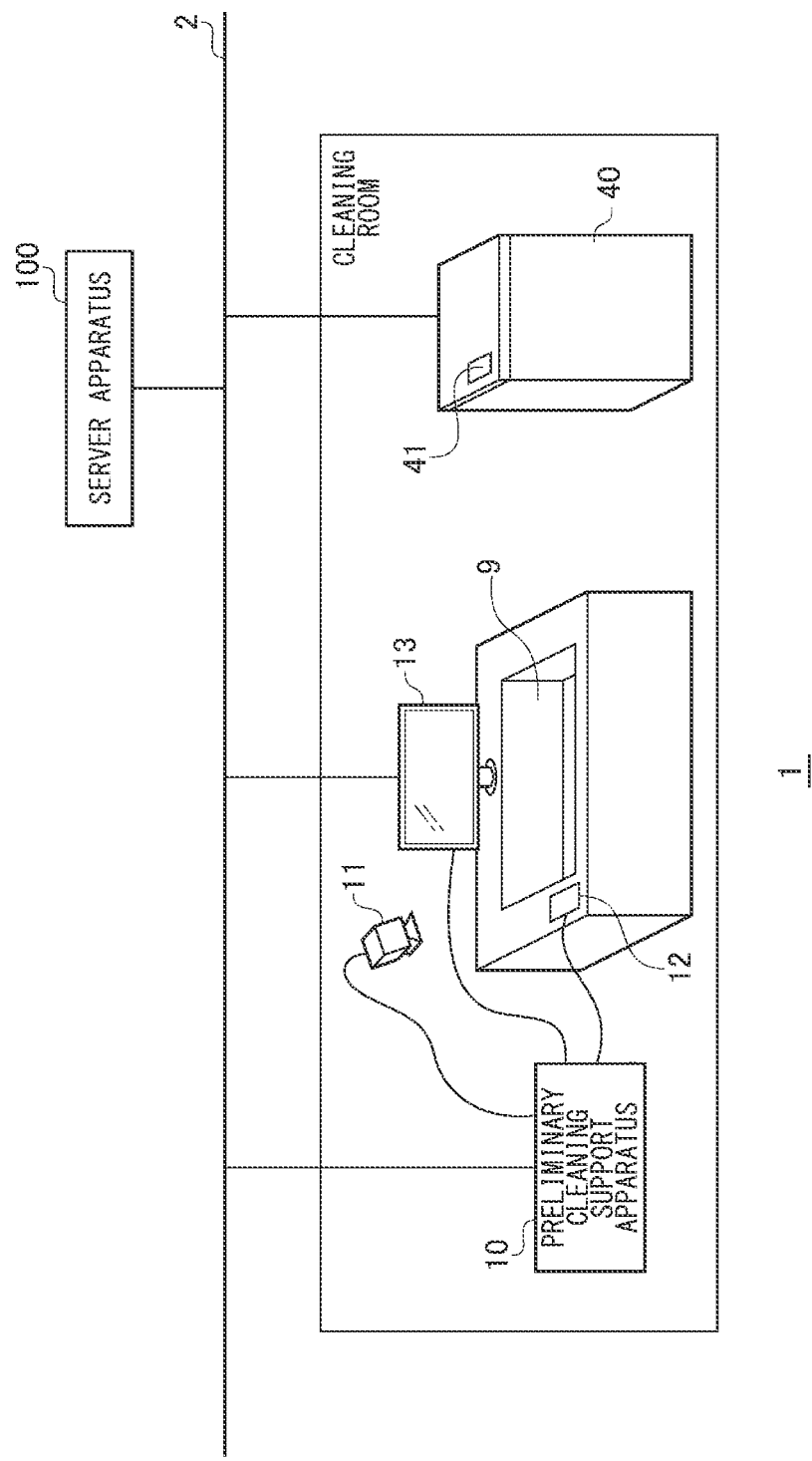
FIG. 1 is a diagram showing the configuration of a cleaning support system according to an embodiment.

FIG. 1 shows the configuration of a cleaning support system 1 according to an embodiment. The cleaning support system 1 is provided in a medical facility such as a hospital and supports endoscopic cleaning by a cleaning worker. The cleaning support system 1 includes a preliminary cleaning support apparatus 10, a cleaning apparatus 40, and a server apparatus 100, and the preliminary cleaning support apparatus 10, the cleaning apparatus 40, and the server apparatus 100 are communicably connected via a network 2 such as a local area network (LAN). FIG. 1 shows one preliminary cleaning support apparatus 10, one cleaning apparatus 40, and one server apparatus 100. Alternatively, there may be a plurality of these apparatuses.

The server apparatus 100 has a database (endoscope DB) in which information on endoscopes used in medical facilities is registered and a database (user DB) in which user information of medical workers such as doctors and cleaning workers is registered. In the endoscope DB, the type and model of an endoscope, the name given in the facility, and the like are recorded in association with identification information (scope ID) for identifying the endoscope. Further, in the user DB, information such as occupation (distinguishing between doctors, workers, or the like), name, age, sex, etc., is recorded in association with identification information (user ID) for identifying the medical worker.

The preliminary cleaning support apparatus 10 has a function of supporting the execution of a manual water leakage test and manual cleaning performed by a cleaning worker. In the following embodiment, the water leakage test and the manual cleaning are collectively referred to as "preliminary cleaning". However, as long as the manual cleaning is included, the preliminary cleaning does not need to include the water leakage test.

The preliminary cleaning support apparatus 10 is connected to an imaging unit 11, an ID reader 12, and an output apparatus 13. The output apparatus 13 is a monitor apparatus including a display and a speaker and is installed near a sink 9. The output apparatus 13 may be a projector or a virtual image display that projects an image. The output apparatus 13 is preferably arranged at a position where the worker who is performing a preliminary cleaning operation can easily see the screen.

In the embodiment, the preliminary cleaning support apparatus 10 is provided as a stationary processing apparatus that is separate from the server apparatus 100. In another example, a preliminary cleaning support function of the preliminary cleaning support apparatus 10 may be mounted in the server apparatus 100. Further, the preliminary cleaning support apparatus 10 may be a portable terminal device such as a tablet device that is equipped with the imaging unit 11 and the output apparatus 13 and that is connected to the ID reader 12.

The cleaning apparatus 40 is an apparatus that performs the main cleaning of an endoscope, has a processing apparatus (not shown) that manages the main cleaning, and is connected to the ID reader 41 for reading a scope ID. The cleaning worker sets an endoscope on which the preliminary cleaning has been performed in a cleaning tank of the cleaning apparatus 40, selects a cleaning program, and performs the main cleaning (mechanical cleaning) of the endoscope.

After the endoscopic examination is completed, the cleaning worker wipes the outer surface of the endoscope and performs a suction cleaning of a suction/forceps channel in the examination room. This cleaning is called a bedside cleaning. The cleaning worker puts the endoscope on which the bedside cleaning has been performed into a dedicated container and carries the dedicated container to the cleaning room.

In the cleaning room, the cleaning worker performs a water leakage test of the endoscope in the sink 9 and manually cleans the endoscope after confirming that there is no water leakage. During the preliminary cleaning, the preliminary cleaning support apparatus 10 preferably displays information indicating the preliminary cleaning procedure on the output apparatus 13 so as to support the preliminary cleaning operation.

The ID reader 12 reads identification information for identifying a subject in a non-contact manner. In the embodiment, the identification information on the subject is recorded in an RFID tag, and the ID reader 12 is an RFID reader that reads the identification information recorded in the RFID tag by short-range wireless communication.

The cleaning worker brings the RFID tag attached to the endoscope close to the ID reader 12 and causes the ID reader 12 to read the scope ID recorded in the RFID tag. The RFID tag may be incorporated as a chip inside the endoscope or may be tied to the endoscope with a string or the like while being housed in a waterproof container. For example, when the ID reader 12 reads the identification information from the RFID tag, the ID reader 12 may generate a sound for giving a notification of the completion of the reading. After hearing the notification sound, the cleaning worker brings the RFID tag, in which the identification information (user ID) for identifying the cleaning worker himself/herself is recorded, close to the ID reader 12 and causes the ID reader 12 to read the user ID.

The ID reader 12 supplies the identification information thus read to the preliminary cleaning support apparatus 10. Although the ID reader 12 is an RFID reader in the embodiment, the ID reader 12 may be a non-contact reader according to another aspect depending on the recording form of the identification information on subjects. For example, the ID reader 12 may be a reader apparatus that reads one-dimensional or two-dimensional code information in a non-contact manner or may be an image processing apparatus that acquires the identification information on the subjects from a camera image.

The imaging unit 11 is installed at a position that allows the cleaning worker to image the state of the preliminary cleaning of an endoscope. The imaging unit 11 is preferably arranged above the sink 9. The imaging unit 11 images a state in which the cleaning worker performs the water leakage test of the endoscope in the sink 9 and also images a state in which the endoscope is manually cleaned using a brush or the like. The imaging unit 11 is a digital camera capable of taking a moving image and may be mounted on the ceiling or wall of the cleaning room with the optical axis direction aligned with the sink 9.

When the preliminary cleaning support apparatus 10 is a portable terminal device such as a tablet device equipped with an imaging unit 11, the portable terminal device may be installed at a position that allows the imaging unit 11 to image the state of the preliminary cleaning of an endoscope. Further, when the preliminary cleaning support apparatus 10 is a wearable terminal device such as a glasses-type device equipped with an imaging unit 11, the wearable terminal device may be mounted at a position that allows the imaging unit 11 to face the front of the cleaning worker's face. The imaging unit 11 supplies the captured image data to the preliminary cleaning support apparatus 10.

The server apparatus 100 collects and accumulates information on cleaning from the preliminary cleaning support apparatus 10 and/or the cleaning apparatus 40. The server apparatus 100 performs various statistical processes based on the accumulated information.

In the cleaning support system 1 according to the embodiment, the preliminary cleaning support apparatus 10 and the server apparatus 100 are provided inside the medical facility. Alternatively, the apparatuses may be provided outside the medical facility. As described above, the function of the preliminary cleaning support apparatus 10 may be mounted in the server apparatus 100. In this case, the server apparatus 100 operates as the preliminary cleaning support apparatus 10.

Figure 2:
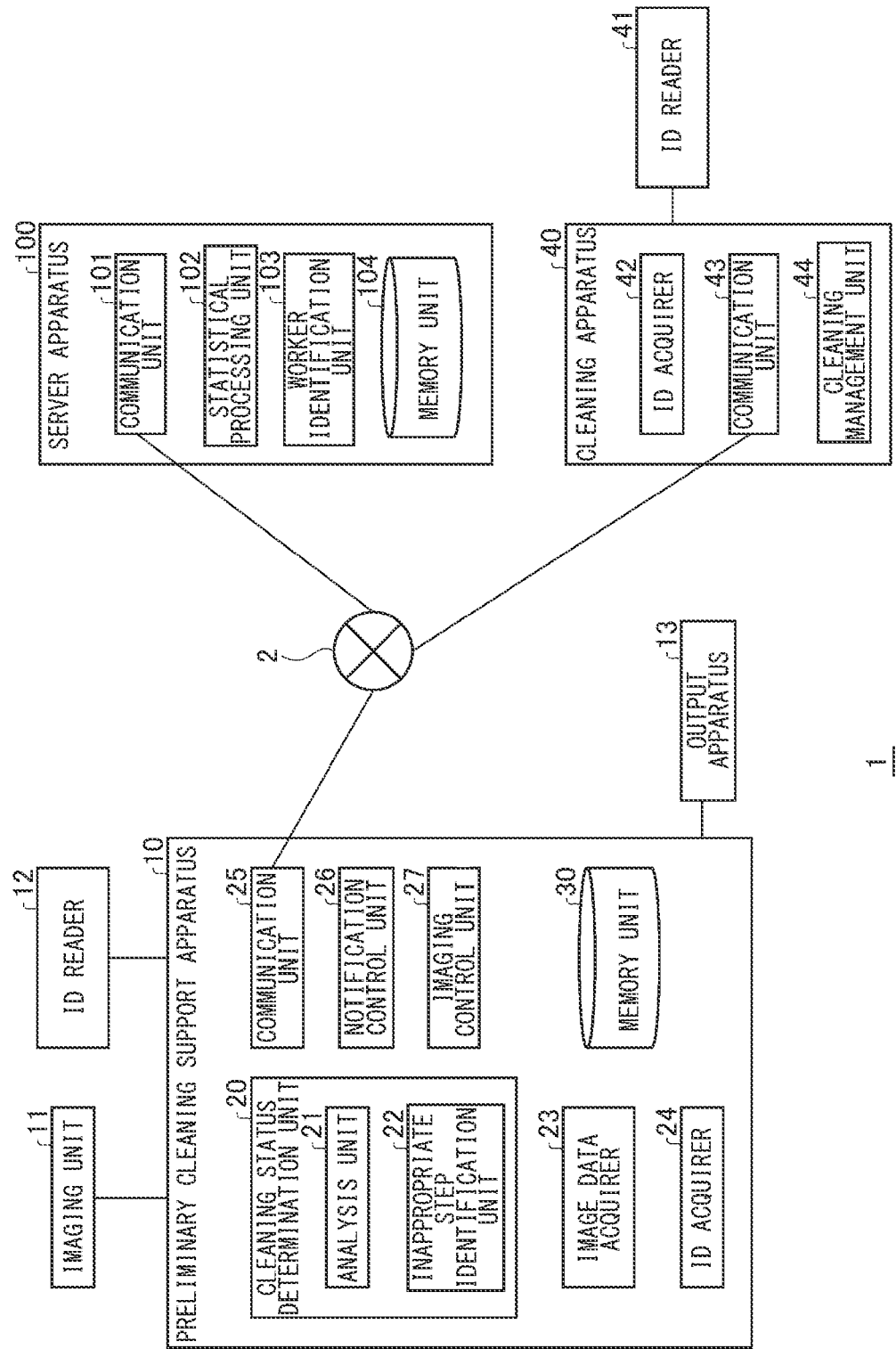
FIG. 2 is a diagram showing functional blocks of the cleaning support system.

FIG. 2 shows functional blocks of the cleaning support system 1. The preliminary cleaning support apparatus 10 has a cleaning status determination unit 20, an image data acquirer 23, an ID acquirer 24, a communication unit 25, a notification control unit 26, an imaging control unit 27, and a memory unit 30. The cleaning apparatus 40 has an ID acquirer 42, a communication unit 43, and a cleaning management unit 44. The cleaning management unit 44 controls the cleaning step of the cleaning apparatus 40. The server apparatus 100 has a communication unit 101, a statistical processing unit 102, a worker identification unit 103, and a memory unit 104. The communication unit 25 in the preliminary cleaning support apparatus 10, the communication unit 43 in the cleaning apparatus 40, and the communication unit 101 in the server apparatus 100 are connected to one another so as to be able to transmit and receive data via the network 2.

The configuration thereof is implemented by hardware such as an arbitrary processor, a memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

Prior to the start of the preliminary cleaning of an endoscope used in an examination, the cleaning worker brings an RFID tag of the endoscope in which the scope ID is recorded and an RFID tag in which the user ID is recorded close to the ID reader 12 and causes the ID reader 12 to read the scope ID and the user ID. When the ID reader 12 reads the scope ID and the user ID, the ID acquirer 24 acquires the scope ID and the user ID.

The memory unit 30 stores procedure information regarding the preliminary cleaning of an endoscope. The procedure information expresses a procedure for the cleaning worker to correctly perform the preliminary cleaning of an endoscope, and the memory unit 30 stores procedure information for each endoscope model. Upon acquiring the scope ID, the ID acquirer 24 makes an inquiry to the endoscope DB of the server apparatus 100 for an endoscope type linked to the scope ID and acquires the scope ID. When the endoscope DB is stored in the memory unit 30, the ID acquirer 24 may acquire the endoscope type linked to the scope ID from the memory unit 30. The notification control unit 26 reads out the procedure information of the endoscope type acquired by the ID acquirer 24 from the memory unit 30 and outputs the procedure information from the output apparatus 13 in a predetermined order.

FIGS. 3 to 6 show examples of procedure information that is output from the output apparatus 13 regarding the preliminary cleaning. The procedure information shown in FIGS. 3 to 6 expresses a part of the entire preliminary cleaning process.

FIG. 3 shows a notification example for a water leakage test procedure. When the ID acquirer 24 acquires the scope ID, the notification control unit 26 displays the procedure information on the water leakage test on the display of the output apparatus 13. This procedure information includes steps A1 to A10. The notification control unit 26 may output the procedure information on the water leakage test shown in FIG. 3 by voice from a speaker.

FIG. 4 shows a notification example for a procedure in the first stage of the manual cleaning. The notification control unit 26 displays the cleaning procedure of the outer surface of the endoscope on the display of the output apparatus 13 along with a reference diagram M. The procedure information for the first stage includes steps B1 to B3.

FIG. 5 shows a notification example for a procedure in the second stage of the manual cleaning. The notification control unit 26 displays a brushing procedure of a suction channel in an insertion part on the display of the output apparatus 13 along with a reference diagram N. The procedure information for the second stage includes steps C1 to C5.

FIG. 6 shows a notification example for a procedure in the third stage of the manual cleaning. The notification control unit 26 displays a brushing procedure of a suction channel in a universal cord on the display of the output apparatus 13 along with the reference diagram N. The procedure information for the third stage includes steps D1 to D5.

The notification control unit 26 causes the output apparatus 13 to display screens shown in FIGS. 3 to 6 in order. The notification control unit 26 may switch the display based on an instruction by a cleaning worker's voice or the like. The displaying of a reference diagram to be worked on along with text data showing the details of the procedure by the output apparatus 13 allows the cleaning worker to intuitively understand the details that require attention. The cleaning worker can use the procedure information displayed on the output apparatus 13 as reference information for correctly performing the preliminary cleaning.

When the ID acquirer 24 acquires the scope ID and the user ID, the imaging control unit 27 supplies an imaging instruction to the imaging unit 11. In response to this imaging instruction, the imaging unit 11 images a state in which the cleaning worker performs the preliminary cleaning on the endoscope. An event other than reading the scope ID and the user ID may cause the imaging control unit 27 to supply the imaging instruction to the imaging unit 11.

For example, the imaging control unit 27 supplies an imaging instruction to the imaging unit 11 in accordance with an instruction from the cleaning worker. When the preliminary cleaning support apparatus 10 has a voice recognition function (not shown), the imaging control unit 27 may receive an imaging instruction by voice from the cleaning worker and supply the imaging instruction to the imaging unit 11. When the preliminary cleaning support apparatus 10 has a line-of-sight detection function (not shown), the cleaning worker may direct the line of sight in a predetermined direction for turning on moving image capturing by the imaging unit 11 so as to thereby cause the imaging control unit 27 to supply an imaging instruction to the imaging unit 11. When the preliminary cleaning support apparatus 10 has a gesture detection function (not shown), the cleaning worker may take a predetermined gesture for turning on the moving image capturing by the imaging unit 11 so as to thereby cause the imaging control unit 27 to supply an imaging instruction to the imaging unit 11. The line-of-sight detection and gesture detection for the cleaning worker may be executed by analyzing an image captured by the imaging unit 11 or may be executed by analyzing an image captured by another imaging unit. When the function of turning on the moving image capturing by the imaging unit 11 is associated with an operation of stepping on a foot pedal (not shown), the cleaning worker may step on the foot pedal so as to thereby cause the imaging control unit 27 to supply an imaging instruction. Further, the imaging control unit 27 may supply an imaging instruction to the imaging unit 11 when the notification control unit 26 outputs the preliminary cleaning procedure from the output apparatus 13.

When the imaging control unit 27 supplies an imaging instruction to the imaging unit 11, the imaging unit 11 captures a moving image of an area including the sink 9. The image data acquirer 23 acquires the captured moving image from the imaging unit 11 and stores the moving image in the memory unit 30. The cleaning worker performs a water leakage test and manual cleaning on the endoscope while looking at the procedure information displayed on the output apparatus 13, and the imaging unit 11 images the state of the water leakage test and the state of the manual cleaning. When the cleaning worker finishes the preliminary cleaning of the endoscope, the cleaning worker inputs the completion of the preliminary cleaning to the preliminary cleaning support apparatus 10. The cleaning worker may input the completion of the preliminary cleaning to the preliminary cleaning support apparatus 10 by operating an operation member such as a foot pedal. The cleaning worker may input the completion of the preliminary cleaning to the preliminary cleaning support apparatus 10 by voice. When the completion of the preliminary cleaning is input, the imaging control unit 27 ends the imaging by the imaging unit 11.

The memory unit 30 stores reference data expressing the correct preliminary cleaning procedure of an endoscope in association with the endoscope type. The reference data is data for analyzing the correctness of the movement of the cleaning work by the worker and may represent a model in which the preliminary cleaning procedure is learned by supervised learning. The cleaning status determination unit 20 uses the reference data so as to analyze image data obtained by imaging the state of the preliminary cleaning by the cleaning worker and determines whether or not preliminary cleaning has been performed on the endoscope.

In the cleaning status determination unit 20, the analysis unit 21 determines whether or not the preliminary cleaning has been performed on the endoscope based on the image data captured by the imaging unit 11. As shown in FIGS. 3 to 6, the preliminary cleaning procedure is defined in detail. However, the analysis unit 21 may determine whether or not the preliminary cleaning has been performed on the endoscope by determining whether or not some typical steps serving as checkpoints have been performed. For example, by image analysis, the analysis unit 21 determines whether or not steps A5, B3, C3, and D3, which serve as checkpoints, have been performed. When it is determined that all the steps, which serve as checkpoints, have been performed, the analysis unit 21 may determine that the endoscope has been manually cleaned.

The analysis unit 21 has artificial intelligence equipped with a human behavior analysis function, analyzes captured image data, and identifies the behavior of the cleaning worker. For example, with regard to the step A5, the analysis unit 21 determines whether or not the cleaning worker is bending a curved part of the endoscope main unit immersed in a container and observing the inside of the container for about 30 seconds at the same time. At this time, if the curved part of the endoscope main unit is not curved, the analysis unit 21 determines that the step A5 is not properly performed. Further, when the observation time is less than 30 seconds, the analysis unit 21 also determines that the step A5 is not properly performed. The analysis unit 21 may have a learned model in which moving image data is learned for each step and determine whether or not each step of the preliminary cleaning has been properly performed based on the image data using the learned model.

The analysis unit 21 may determine whether or not all the steps in the preliminary cleaning have been performed. The analysis unit 21 determines that the preliminary cleaning has been properly performed on the endoscope by determining that all the steps have been performed correctly.

Shown in the following are specific exemplary methods for determining whether or not the steps of the preliminary cleaning have been properly performed.
(a) When the reference value of the amount of strokes in the advancing/retreating range of a cleaning brush is set in the steps, the analysis unit 21 compares the amount of strokes of the cleaning brush in the moving image with the reference value and determines whether or not the amount of strokes is proper.
(b) When the number of advancing/retreating times of the cleaning brush is set in the steps, the analysis unit 21 counts the number of advancing/retreating times of the cleaning brush included in the moving image and determines whether or not the brushing is proper.
(c) When a reference value is set for an angle at which the cleaning brush reciprocates in the steps, the analysis unit 21 compares the reciprocating angle with the reference value and determines whether or not the angle is a proper angle. For example, in the step C2, it is defined that a channel cleaning brush is inserted at an angle of 45 degrees with respect to the suction cylinder opening, and the analysis unit 21 determines that an insertion angle is not a proper angle if the insertion angle is around 45 degrees.
(d) When the shape of the cleaning brush used in the steps is not a reference shape, the analysis unit 21 determines that an appropriate brush is not being used.

As described above, the analysis unit 21 determines whether or not each step of the preliminary cleaning is properly carried out by image-analyzing the moving image data in each step carried out by the cleaning worker. An inappropriate step identification unit 22 receives a determination result from the analysis unit 21 and identifies a step that has not been properly performed. The inappropriate step identification unit 22 notifies the notification control unit 26 of information indicating the identified step.

The notification control unit 26 generates notification data regarding the determination result in the cleaning status determination unit 20 and outputs the notification data from the output apparatus 13. Upon receiving information indicating the step that has not been properly performed from the inappropriate step identification unit 22, the notification control unit 26 generates notification data including information on the step and outputs the notification data from the output apparatus 13.

Figures 7, 8:
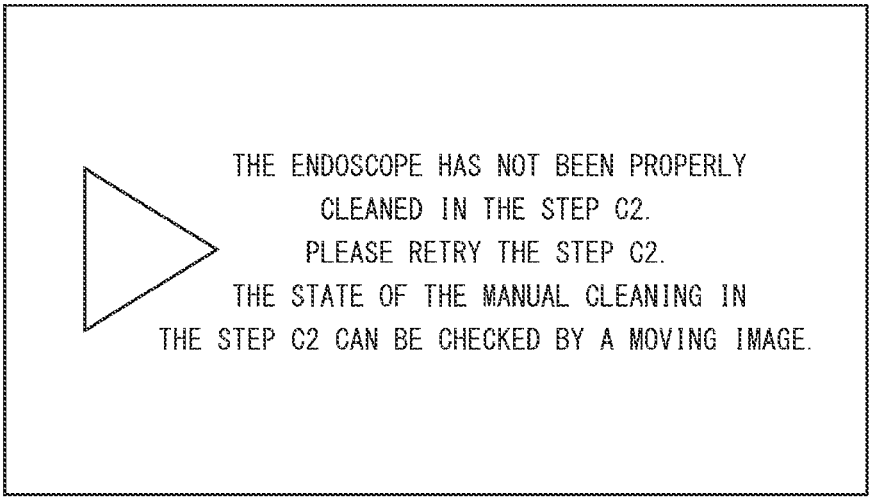
FIG. 7 is a diagram showing a notification example for warning with regard to a manual cleaning step of an endoscope.
FIG. 8 is a diagram showing another notification example for warning with regard to the manual cleaning step of an endoscope.

FIG. 7 shows a notification example for warning with regard to a manual cleaning step of an endoscope. The notification control unit 26 generates notification data in text and outputs the notification data from the output apparatus 13, and the output apparatus 13 displays a warning in text on the display. The output apparatus 13 may output text data by voice. This allows the cleaning worker to recognize the existence of an inappropriate step in the manual cleaning of the endoscope and start a specified step over again.

FIG. 8 shows another notification example for warning with regard to a manual cleaning step of an endoscope. The notification control unit 26 generates notification data and outputs the notification data from the output apparatus 13. The notification control unit 26 generates notification data including image data obtained by imaging the state of a step that has not been properly performed. The notification control unit 26 extracts the captured image data of the state of the step determined to be inappropriate from captured image data stored in the memory unit 30 and outputs the image data from the output apparatus 13.

When the cleaning worker operates a play button, the output apparatus 13 reproduces the captured image data of the step C2. At this time, the text data "Tilt the channel cleaning brush 45 degrees to the suction cylinder opening on the side wall of the suction cylinder and insert it in the direction of the insertion part (arrow A in a reference figure N). Push the brush part out of the exit of the endoscope tip forceps" for the step C2 shown in FIG. 5 may be displayed along with a moving image. Based on the moving image of the step C2 and the text data of the step C2, the cleaning worker recognizes that the channel cleaning brush is not inserted at an angle of 45 degrees and executes the step C2 again while paying attention to the insertion angle.

Figure 9:
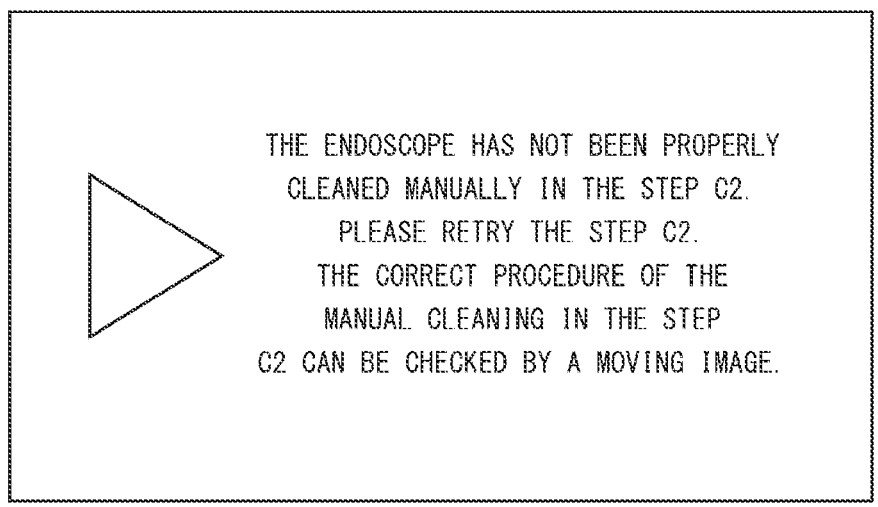
FIG. 9 is a diagram showing another notification example for warning with regard to the manual cleaning step of an endoscope.

FIG. 9 shows another notification example for warning with regard to a manual cleaning step of an endoscope. The notification control unit 26 generates notification data and outputs the notification data from the output apparatus 13. The notification control unit 26 generates notification data including image data obtained by imaging a state in which a step of the preliminary cleaning that has not been properly performed is properly performed. The image data obtained by imaging the state in which the step is properly performed may be a moving image in which the step is properly performed by a different worker or the worker himself/herself in the past. The notification control unit 26 acquires model moving image data of the step C2 stored in the memory unit 104 of the server apparatus 100 and outputs the model moving image data from the output apparatus 13.

When the cleaning worker operates a play button, the output apparatus 13 reproduces the moving image data serving as a model of the step C2. At this time, the text data "Tilt the channel cleaning brush 45 degrees to the suction cylinder opening on the side wall of the suction cylinder and insert it in the direction of the insertion part (arrow A in the reference figure N). Push the brush part out of the exit of the endoscope tip forceps" for the step C2 shown in FIG. 5 may be displayed along with a moving image. Based on the moving image of the step C2 and the text data of the step C2, the cleaning worker recognizes that the channel cleaning brush should be inserted at an angle of 45 degrees and executes the step C2 again while paying attention to the insertion angle.

When the analysis unit 21 determines that the preliminary cleaning has not been performed on the endoscope, the notification control unit 26 may generate notification data including information indicating risks that may occur when the endoscope is cleaned by the cleaning apparatus 40 without going through a proper preliminary cleaning and output the notification data from the output apparatus 13. The notification control unit 26 may generate text data stating "Because the manual cleaning has not been properly performed on the endoscope, cleaning by the cleaning apparatus may become insufficient" as notification data indicating the risks.

As described above, when the analysis unit 21 determines that the preliminary cleaning has not been performed properly on the endoscope, the notification control unit 26 generates notification data indicating that the preliminary cleaning has not been performed properly on the endoscope. Upon being informed of this notification data from the output apparatus 13, the cleaning worker is given an opportunity to promptly re-clean the endoscope. When the notification control unit 26 displays a notification screen on the output apparatus 13, at least one of voice and light may be generated from the output apparatus 13 so as to make the cleaning worker notice that the notification screen is displayed.

When the analysis unit 21 determines that the preliminary cleaning has been properly performed on the endoscope, the notification control unit 26 may generate notification data indicating that the preliminary cleaning has been properly performed on the endoscope and output the notification data from the output apparatus 13. This allows the cleaning worker to recognize that the preliminary cleaning has been properly performed.

Figure 10:
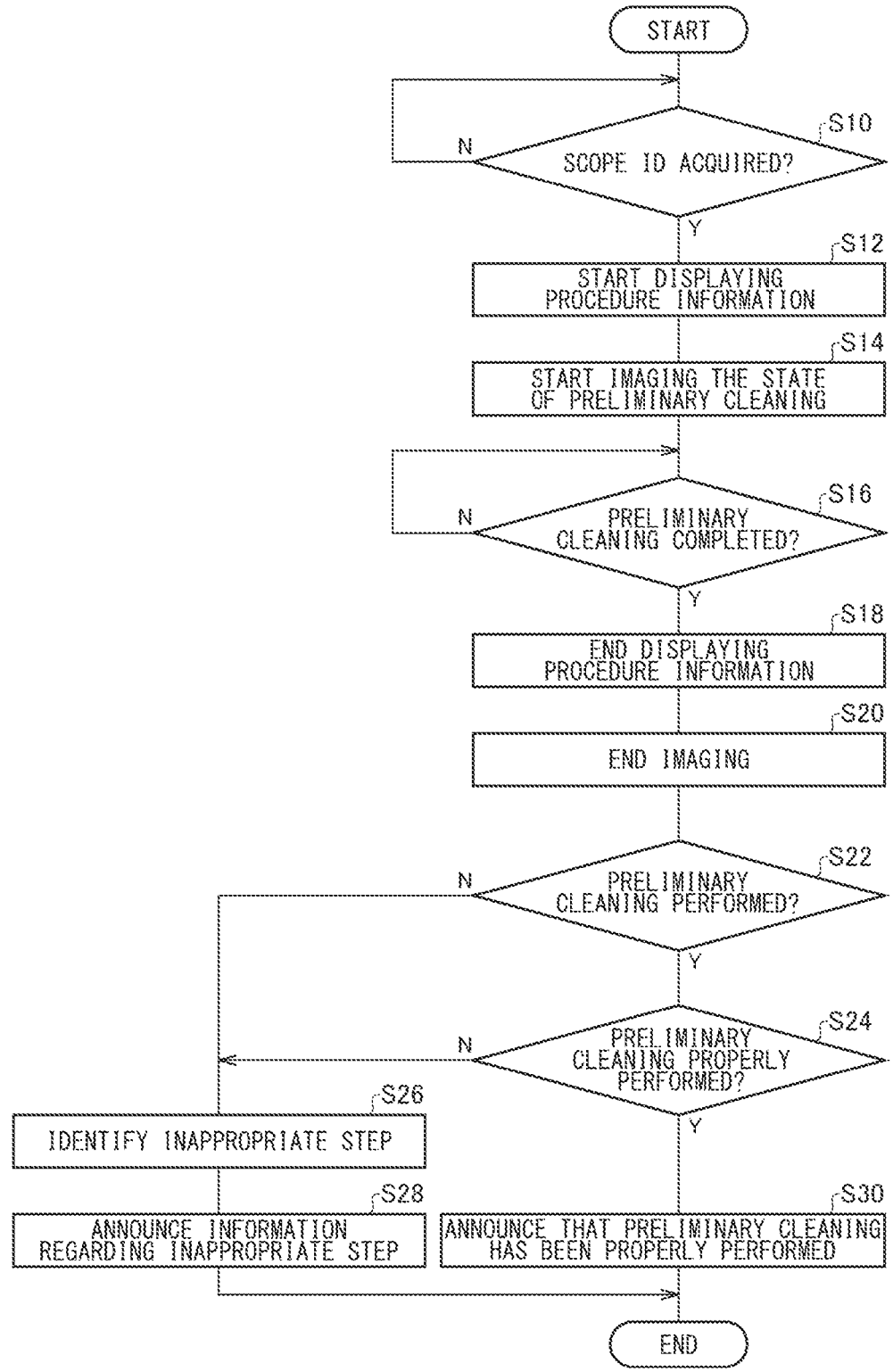
FIG. 10 is a flowchart showing a preliminary cleaning support process.

FIG. 10 is a flowchart showing a preliminary cleaning support process. The ID acquirer 24 waits for the scope ID to be read by the ID reader 12 (N in S10). When the ID reader 12 reads the scope ID and the ID acquirer 24 acquires the scope ID (Y in S10), the notification control unit 26 outputs the procedure information for the endoscope type linked to the scope ID from the output apparatus 13 (S12). Further, the imaging control unit 27 controls the imaging unit 11 to start the imaging of the state of the preliminary cleaning of the endoscope (S14). The output of the procedure information by the output apparatus 13 and the image capturing by the imaging unit 11 are performed until the completion of the preliminary cleaning is input to the preliminary cleaning support apparatus 10 (N in S16).

When the completion of the preliminary cleaning is input to the preliminary cleaning support apparatus 10 (Y in S16), the notification control unit 26 ends the output of the procedure information (S18), and the imaging control unit 27 ends the imaging by the imaging unit 11 (S20).

The cleaning status determination unit 20 determines whether or not the preliminary cleaning has been performed based on the image data obtained by the imaging of the state of the preliminary cleaning (S22). When it is determined that the preliminary cleaning has not been performed on the endoscope (N in S22), the cleaning status determination unit 20 identifies the step of the preliminary cleaning that has not been performed (S26), and the notification control unit 26 outputs information on the step of the preliminary cleaning that has not been performed from the output apparatus 13 (S28). On the other hand, when it is determined that the preliminary cleaning has been performed on the endoscope (Y in S22), the cleaning status determination unit 20 determines whether or not the preliminary cleaning has been performed properly on the endoscope (S24).

When it is determined that the preliminary cleaning has not been properly performed on the endoscope (N in S24), the cleaning status determination unit 20 identifies the step of the preliminary cleaning that has not been properly performed (S26), and the notification control unit 26 outputs information on the step of the preliminary cleaning that has not been properly performed from the output apparatus 13 (S28). On the other hand, when it is determined that the preliminary cleaning has been properly performed on the endoscope (Y in S24), the notification control unit 26 outputs information indicating that the preliminary cleaning has been properly performed on the endoscope from the output apparatus 13 (S30).

The information indicating the cleaning status determination result in the cleaning status determination unit 20 is transmitted to the cleaning apparatus 40 and the server apparatus 100 as information regarding the determination result along with information indicating the start time and completion time of the preliminary cleaning and the scope ID. In the cleaning apparatus 40, the communication unit 43 receives the information regarding the determination result and supplies the information to the cleaning management unit 44.

As described above, when the analysis unit 21 determines that the preliminary cleaning has not been performed on the endoscope, the notification control unit 26 generates notification screen data and outputs the notification screen data from the output apparatus 13. By looking at the notification screen, the cleaning worker recognizes that the cleaning step has been inappropriate and re-cleans the endoscope. However, if the cleaning worker does not notice the display on the notification screen, he/she will carry the endoscope to the cleaning apparatus 40 and try to perform the main cleaning. Hereinafter, the operation of the cleaning apparatus 40 when the analysis unit 21 determines that the preliminary cleaning has not been properly performed on the endoscope will be described.

The cleaning worker brings the RFID tag attached to the endoscope close to the ID reader 41 of the cleaning apparatus 40 and causes the ID reader 41 to read the scope ID recorded in the RFID tag. The ID acquirer 42 acquires the scope ID and supplies the scope ID to the cleaning management unit 44. The cleaning management unit 44 compares the scope ID transmitted from the preliminary cleaning support apparatus 10 with the scope ID acquired by the ID acquirer 42. When the scope IDs match and the information indicating the determination result indicates that the preliminary cleaning has not been properly performed on the endoscope, the cleaning management unit 44 limits the start of the cleaning step. That is, even when a cleaning start button of the cleaning apparatus 40 is operated by the cleaning worker, the cleaning management unit 44 treats this operation as an invalid operation. The cleaning management unit 44 may announce that the main cleaning cannot be started because the preliminary cleaning is inappropriate from a notification unit (not shown) of the cleaning apparatus 40.

Next, the operation of the cleaning apparatus 40 when the analysis unit 21 determines that the preliminary cleaning has been properly performed on the endoscope will be described. When the cleaning worker causes the ID reader 41 to read the RFID tag attached to the endoscope, the ID acquirer 42 acquires the scope ID and supplies the scope ID to the cleaning management unit 44. The cleaning management unit 44 compares the scope ID transmitted from the preliminary cleaning support apparatus 10 with the scope ID acquired by the ID acquirer 42. When the scope IDs match and the information indicating the determination result indicates that the preliminary cleaning has been properly performed on the endoscope, the cleaning management unit 44 compares the current time with the preliminary cleaning completion time. When the preliminary cleaning completion time in the preliminary cleaning support apparatus 10 is earlier than the current time by a predetermined time or more, the preliminary cleaning is preferably performed again on the endoscope. Therefore, when the time difference between the current time and the preliminary cleaning completion time is within a predetermined time (for example, 24 hours), the cleaning management unit 44 does not limit the start of the cleaning step and starts the cleaning step by the operation of the cleaning start button. On the other hand, if the time difference between the current time and the preliminary cleaning completion time exceeds the predetermined time, the cleaning management unit 44 preferably limits the start of the cleaning step.

The server apparatus 100 collects information regarding cleaning from the preliminary cleaning support apparatus 10 and the cleaning apparatus 40 and performs a statistical process. The communication unit 101 receives information regarding the determination result in the cleaning status determination unit 20 from the communication unit 25 of the preliminary cleaning support apparatus 10. The information regarding the determination result includes the scope ID, the user ID, the preliminary cleaning start time, and the preliminary cleaning completion time in addition to the information indicating the determination result of whether or not the preliminary cleaning step is appropriate. The information regarding the determination result may further include captured image data. The memory unit 104 stores the information regarding the determination result of the preliminary cleaning as preliminary cleaning history. Instead of storing all the information regarding the determination result as the preliminary cleaning history, the memory unit 104 may store at least one of the scope ID and the user ID in association with the information indicating the determination result in the cleaning status determination unit 20.

The communication unit 101 receives information regarding the main cleaning from the communication unit 43 of the cleaning apparatus 40. The information regarding the main cleaning includes a scope ID, a cleaning apparatus ID, a user ID, a main cleaning start time, and a main cleaning completion time. The memory unit 104 stores the information regarding the main cleaning as main cleaning history.

The statistical processing unit 102 generates a statistical value regarding a frequency at which it is determined that the preliminary cleaning has not been properly performed on the endoscope based on the preliminary cleaning history stored in the memory unit 104. For example, the statistical processing unit 102 may generate a statistical value regarding the frequency at which it is determined that the preliminary cleaning has not been properly performed on the endoscope for each user ID. This statistical value serves as an index indicating whether the cleaning worker can properly perform the preliminary cleaning on the endoscope. In this example, the statistical value represents a preliminary cleaning failure rate. A high statistical value indicates that the cleaning worker cannot perform the preliminary cleaning on the endoscope in a correct procedure, and a low statistical value indicates that the cleaning worker can perform the preliminary cleaning on the endoscope in the correct procedure. By generating such a statistical value, the preliminary cleaning skill of the worker can be objectively evaluated.

The worker identification unit 103 acquires the statistical value for each worker generated by the statistical processing unit 102 and identifies a worker having a low preliminary cleaning skill and a worker having a high preliminary cleaning skill. The worker identification unit 103 may identify the user ID of the cleaning worker whose calculated statistical value is larger than a first threshold value and/or the user ID of the cleaning worker whose calculated statistical value is smaller than a second threshold value. A cleaning worker whose calculated statistical value is larger than the first threshold value is a worker with a low preliminary cleaning skill, and a cleaning worker whose calculated statistical value is smaller than the second threshold value is a worker with a high preliminary cleaning skill. The second threshold value is smaller than the first threshold value. The communication unit 101 transmits the user ID identified by the worker identification unit 103 to the preliminary cleaning support apparatus 10.

In the preliminary cleaning support apparatus 10, when the communication unit 25 receives the user ID of a worker with a high preliminary cleaning skill and/or a worker with a low preliminary cleaning skill, the preliminary cleaning support apparatus 10 supplies the user ID to the image data acquirer 23. The image data acquirer 23 uses the supplied user ID as a transfer condition for moving image data.

Before the start of the preliminary cleaning of the endoscope, when the ID reader 12 acquires the user ID of the cleaning worker, the image data acquirer 23 determines whether the acquired user ID matches the user ID supplied from the server apparatus 100. When the acquired user ID matches the user ID supplied from the server apparatus 100, the worker is a worker with a high preliminary cleaning skill or a worker with a low preliminary cleaning skill.

A moving image of the preliminary cleaning work of a worker with a high preliminary cleaning skill serves as a learning material for beginners of cleaning work and workers with a low preliminary cleaning skill. Further, a moving image of the preliminary cleaning work of a worker with a low preliminary cleaning skill serves as a material for educating the worker. Therefore, the image data acquirer 23 transfers acquired image data to the server apparatus 100 in order to use the image data for education. The memory unit 104 may store image data that is transmitted as reference image data.

The memory unit 104 may store information indicating the step identified by the inappropriate step identification unit 22 of the preliminary cleaning support apparatus 10. As described above, the communication unit 25 transmits the information regarding the determination result in the cleaning status determination unit 20 to the server apparatus 100. Along with the information, the communication unit 25 may transmit information indicating a step of the preliminary cleaning that has not been properly performed at this time. This allows the memory unit 104 to store information indicating the step determined to be inappropriate. The statistical processing unit 102 may generate a statistical value regarding a frequency at which it is determined that the preliminary cleaning has not been properly performed based on the information stored in the memory unit 104. When the statistical processing unit 102 generates a statistical value based on a step, the statistical value is used, for example, to identify a step in which a procedure error is likely to occur.

FIG. 11 shows an example of information stored in the memory unit 104. The patient ID is identification information that identifies a subject to be examined. The scope ID is the identification information of an endoscope used for the examination and then subjected to the preliminary cleaning and the main cleaning. The worker ID is the identification information of the user who has performed the preliminary cleaning and the main cleaning. When the worker of the preliminary cleaning and the worker of the main cleaning are different, the user IDs of the workers who have performed the respective cleanings may be stored. The image data is image data captured in the preliminary cleaning.

The memory unit 104 preferably stores at least one of the patient ID, the scope ID, and the worker ID in association with the image data. In the example shown in FIG. 11, the memory unit 104 stores a patient ID, a scope ID, a worker ID, an examination start time, an examination completion time, a preliminary cleaning start time, a preliminary cleaning completion time, a main cleaning start time, a main cleaning completion time, and an image data in association with an examination number. The memory unit 104 stores at least one of the patient ID, the scope ID, and the worker ID in association with the image data. Thereby, it can be checked later that the preliminary cleaning has been properly performed on the endoscope through the moving image.

Described above is an explanation based on the embodiments of the present disclosure. The embodiments are intended to be illustrative only, and it will be obvious to those skilled in the art that various modifications to constituting elements and processes thereof could be developed and that such modifications are also within the scope of the present disclosure.

In the embodiment, it has been described that the imaging unit 11 images the sink 9. Alternatively, the cleaning worker may wear a wearable terminal with an image capturing function, and the wearable terminal may image the sink 9. The wearable terminal may have an output apparatus 13, transmit captured image data to the preliminary cleaning support apparatus 10, and output notification data generated by the preliminary cleaning support apparatus 10 from the output apparatus 13. The wearable terminal may be formed to have the function of the preliminary cleaning support apparatus 10.

In the embodiment, a case where the cleaning status determination unit 20 and the notification control unit 26 are mounted in one processing apparatus has been described. However, the cleaning status determination unit 20 and the notification control unit 26 may be mounted in different processing apparatuses. For example, one of the cleaning status determination unit 20 and the notification control unit 26 may be provided inside a medical facility, and the other may be provided outside the medical facility.

In the embodiment, the cleaning status determination unit 20 analyzes captured image data after the completion of the preliminary cleaning so as to determine the cleaning status. In an exemplary variation, the cleaning status determination unit 20 may analyze the image data in real time so as to determine the cleaning status.

In the embodiment, it has been described that the server apparatus 100 manages the cleaning history. Alternatively, the preliminary cleaning support apparatus 10 may manage the cleaning history.

What is claimed is:

1. A cleaning support system that supports cleaning of an endoscope, comprising:
   a display device; and
   one or more processors comprising hardware, wherein the one or more processors are configured to:
      acquire image data obtained by imaging a state of preliminary cleaning of the endoscope;
      input the image data to a learned model, recorded in a memory, in which a procedure of the preliminary cleaning has been learned so as to determine whether or not the preliminary cleaning of the endoscope has been properly performed;
      identify a step of the preliminary cleaning that has not been properly performed; and
      display notification data including information regarding the step of the preliminary cleaning that has not been properly performed on the display device.

2. The cleaning support system according to claim 1, wherein
   the memory records the learned model in which the procedure of each step of the preliminary cleaning has been learned, and
   the one or more processors are configured to determine whether or not each step of the preliminary cleaning has been properly performed using the learned model.

3. The cleaning support system according to claim 2, wherein the one or more processors are configured to determine that the step of the preliminary cleaning has not been properly performed if observation made by a cleaning worker is imaged in the image data while a curved part of the endoscope immersed in a container is in an unbent state.

4. The cleaning support system according to claim 2, wherein the one or more processors are configured to:
   determine whether or not all the steps in the preliminary cleaning have been properly performed; and determine that the preliminary cleaning has been properly performed when all the steps have been properly performed.

5. The cleaning support system according to claim 2, wherein the one or more processors are configured to determine whether or not the step of the preliminary cleaning has been properly performed based on movement or shape of a brush imaged in the image data.

6. The cleaning support system according to claim 1, wherein the one or more processors are configured to:
acquire a scope ID of the endoscope; and
display cleaning procedure information for an endoscope type linked to the scope ID on the display device.

7. The cleaning support system according to claim 1, wherein the one or more processors are configured to:
store the information regarding the step of the preliminary cleaning that has not been properly performed in the memory when it is determined that the preliminary cleaning of the endoscope has not been properly performed;
based on the stored information, generate for each cleaning worker a statistical value regarding a frequency at which it is determined that the preliminary cleaning has not been properly performed; and
identify a cleaning worker having a high preliminary cleaning skill and a cleaning worker having a low preliminary cleaning skill based on the statistical value.

8. The cleaning support system according to claim 1, including a cleaning apparatus, wherein the one or more processors are configured to limit the start of the cleaning of the endoscope performed by the cleaning apparatus if the preliminary cleaning of the endoscope has not been properly performed.

9. A cleaning support method that supports cleaning, comprising:
acquiring image data obtained by imaging a state of preliminary cleaning of an endoscope;
inputting the image data to a learned model, recorded in a memory, in which a procedure of the preliminary cleaning has been learned so as to determine whether or not the preliminary cleaning of the endoscope has been properly performed;
displaying a step of the preliminary cleaning that has not been properly performed; and
displaying notification data on a display device including information regarding the step of the preliminary cleaning that has not been properly performed.

10. The cleaning support method according to claim 9, wherein
the memory records the learned model in which the procedure of each step of the preliminary cleaning has been learned, further comprising:
determining whether or not each step of the preliminary cleaning has been properly performed using the learned model.

11. The cleaning support method according to claim 10, further comprising determining that the step of the preliminary cleaning has not been properly performed if observation made by a cleaning worker is imaged in the image data while a curved part of the endoscope immersed in a container is in an unbent state.

12. The cleaning support method according to claim 10, further comprising:
determining whether or not all the steps in the preliminary cleaning have been properly performed; and
determining that the preliminary cleaning has been properly performed when all the steps have been properly performed.

13. The cleaning support method according to claim 10, further comprising determining whether or not the step of the preliminary cleaning has been properly performed based on movement or shape of a brush imaged in the image data.

14. The cleaning support method according to claim 9, further comprising:
acquiring a scope ID of the endoscope; and
displaying cleaning procedure information for an endoscope type linked to the scope ID on the display device.

15. The cleaning support method according to claim 9, further comprising:
storing the information regarding the step of the preliminary cleaning that has not been properly performed in the memory when it is determined that the preliminary cleaning of the endoscope has not been properly performed;
based on the stored information, generating for each cleaning worker a statistical value regarding a frequency at which it is determined that the preliminary cleaning has not been properly performed; and
identifying a cleaning worker having a high preliminary cleaning skill and a cleaning worker having a low preliminary cleaning skill based on the statistical value.

16. A cleaning support system that supports cleaning of an endoscope, comprising:
a display device;
a camera; and
one or more processors comprising hardware, wherein the one or more processors are configured to:
acquire image data obtained by imaging a state of preliminary cleaning of the endoscope from the camera;
determine whether or not the preliminary cleaning has been performed on the endoscope based on the image data;
identify a step of the preliminary cleaning that has not been properly performed based on the image data;
generate notification data including information regarding the step of the preliminary cleaning that has not been properly performed;
control the display device to display the notification data;
store the information regarding the step of the preliminary cleaning that has not been properly performed in a memory when it is determined that the preliminary cleaning has not been properly performed on the endoscope;
based on the stored information, generate for each cleaning worker a statistical value regarding a frequency at which it is determined that the preliminary cleaning has not been properly performed; and
identify a cleaning worker having a high preliminary cleaning skill and a cleaning worker having a low preliminary cleaning skill based on the statistical value;
wherein the memory records a learned model in which a procedure of each step of the preliminary cleaning has been learned, and
the one or more processors are configured to determine whether or not each step of the preliminary cleaning has been properly performed using the learned model.

17. The cleaning support system according to claim 16, wherein the one or more processors are configured to determine that the step of the preliminary cleaning has not been properly performed if observation made by the cleaning worker is imaged in the image data while a curved part of the endoscope immersed in a container is in an unbent state.

18. The cleaning support system according to claim 16, wherein the one or more processors are configured to:
   determine whether or not all the steps in the preliminary cleaning have been properly performed; and
   determine that the preliminary cleaning has been properly performed when all the steps have been properly performed.

19. The cleaning support system according to claim 16, wherein the one or more processors are configured to determine whether or not the step of the preliminary cleaning has been properly performed based on movement or shape of a brush imaged in the image data.

20. The cleaning support system according to claim 16, wherein the one or more processors are configured to:
   acquire a scope ID of the endoscope; and
   display cleaning procedure information for an endoscope type linked to the scope ID on the display device.

21. The cleaning support system according to claim 16, including a cleaning apparatus, wherein the one or more processors are configured to limit the start of the cleaning of the endoscope performed by the cleaning apparatus if the preliminary cleaning of the endoscope has not been properly performed.

* * * * *